US00PP27531P2

(12) United States Plant Patent
NeSmith

(10) Patent No.: US PP27,531 P2
(45) Date of Patent: Jan. 10, 2017

(54) SOUTHERN HIGHBUSH BLUEBERRY PLANT NAMED 'TH-917'

(50) Latin Name: *Vaccinium corymbosum*
Varietal Denomination: TH-917

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/545,947

(22) Filed: Jul. 10, 2015

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

PUBLICATIONS

Smith S. Blueberry Cultivar Development at The University of Georgia A progress Report for 2012.*

* cited by examiner

*Primary Examiner* — Annette Para
(74) *Attorney, Agent, or Firm* — Klarquist Sparkman, LLP

(57) ABSTRACT

The new variety 'TH-917' is provided. The new and distinct variety ripens around mid May in southern Georgia and late May in middle Georgia. The fruit of the new variety 'TH-917' are large, firm, have good flavor and scar. The new variety 'TH-917' is vigorous with an estimated chilling requirement of about 500 to 550 hours at or below approximately 7° C. The asexually reproduced variety is reliably propagated vegetatively.

5 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TH-917' is a southern highbush blueberry plant that is a *Vaccinium corymbosum.*

Variety denomination: The new southern highbush blueberry plant claimed is of the variety denominated 'TH-917'.

BACKGROUND OF THE INVENTION

The present invention relates to the discovery of a new and distinct cultivar of southern highbush blueberry plant botanically known as a *Vaccinium corymbosum* and herein referred to as 'TH-917', as herein described and illustrated.

The new blueberry plant variety 'TH-917' was selected in Griffin, Ga., in 2005. The new variety 'TH-917' ripens around mid-May in southern Georgia to late May in middle Georgia. The fruit of the new variety 'TH-917' are firm with good flavor and favorable scar. The new variety 'TH-917' has good yield and is vigorous with an estimated chilling requirement of about 500-550 hours at or below 7° C.

Pedigree and history: 'TH-917' was selected in 2005 at the Georgia Experiment Station in Griffin, Ga., originating from a cross of 'TH-653'×'Millennia' made by Dr. D. Scott NeSmith in 2002. The maternal parent ('TH-653') is a non-patented UGA breeding line derived from a cross of 'Legacy'×'TH-454'. Both 'Legacy' and 'TH-454' are not patented. The paternal parent, 'Millennia', is the subject of U.S. Plant Pat. No. 12,816. The selection 'TH-917' has been tested in asexually propagated (by vegetative cuttings) plantings at UGA Blueberry Research Farms in Alapaha and Griffin, Ga. since 2007.

SUMMARY OF THE INVENTION

The new blueberry plant variety 'TH-917' has not been observed under all possible environmental conditions. The phenotype may vary somewhat with variations in environment and cultural practices such as temperature and light intensity without, however, any variance in genotype.

The following traits have been repeatedly observed in asexually propagated plants of the new cultivar growing in Alapaha and Griffin, Ga., and are determined to be unique firmly fixed characteristics of the new blueberry plant variety 'TH-917':

1. Favorable scar;
2. Very good storage quality;
3. Excellent berry flavor;
4. Good fruit firmness.

The new variety 'TH-917' can be compared to the southern highbush blueberry variety 'Camellia' (the subject of U.S. Plant Pat. No. 18,151).

Comparison: The selection 'TH-917' flowers and ripens with 'Camellia' in the mid-to-late Georgia southern highbush season. 'TH-917' has large, firm berries with good flavor as compared to standards 'Star' (U.S. Plant Pat. No. 10,675) and 'Camellia' in Alapaha and Griffin, Ga. over a 5-year period (Tables 1 and 2). Table 3 describes yield, and berry weight, firmness and Brix for 'TH-917' as compared to the 'Star' and 'Camellia' southern highbush blueberry cultivars, for the years 2010-2013. 'TH-917' had better berry firmness than 'Camellia' and a lower firmness than 'Star'. 'TH-917' is highly vigorous like 'Camellia' but does not have the same issues of "leggyness". Major attractions of 'TH-917' are high fruit quality and the ability to compliment 'Camellia' in filling the mid to late May production gap in southern Georgia. Preliminary studies suggest that 'TH-917' has excellent fruit holding and/or storage quality, and may also be suitable for machine harvesting.

TABLE 1

5-year average ratings of some fruit and plant characteristics of 'TH-917' and southern highbush standard cultivars 'Star' and 'Camellia' from 2009-2013 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in Fall 2007.

| | Alapaha location | | |
|---|---|---|---|
| Berry and plant attributes[1/] | 'Star' | 'Camellia' | 'TH-917' |
| Berry size | 7.6 ± 0.2 | 8.9 ± 0.2 | 7.9 ± 0.3 |
| Berry scar | 7.0 ± 0.1 | 7.2 ± 0.2 | 7.5 ± 0.2 |
| Berry color | 7.1 ± 0.1 | 8.7 ± 0.2 | 7.6 ± 0.2 |
| Berry firmness | 7.2 ± 0.1 | 7.2 ± 0.1 | 7.8 ± 0.1 |
| Berry flavor | 7.0 ± 0.1 | 7.8 ± 0.1 | 7.5 ± 0.2 |
| Cropping | 4.7 ± 1.7 | 5.4 ± 0.3 | 5.9 ± 0.5 |
| Plant vigor | 6.3 ± 0.2 | 9.8 ± 0.2 | 8.5 ± 0.4 |
| Date of 50% flowering | March 3 | March 11 | March 10 |
| Date of 50% ripening | May 8 | May 15 | May 17 |
| Fruit development period (days) | 66.3 ± 6.1 | 65.3 ± 4.9 | 67.0 ± 3.8 |

[1/]Values are means ± the standard error with n = 5.

TABLE 2

5-year average ratings of some fruit and plant characteristics of 'TH-917' and southern highbush standard cultivars 'Star' and 'Camellia' (2009-2013) in field test plots at Griffin, GA. Rating scales are based on a 1 to 10 score, with 1 being the least desirable and 10 being the most desirable. A value of 6-7 is generally considered to be the minimum acceptable rating for a commercial cultivar. These plants were established in Fall 2007.

| | Griffin location | | |
|---|---|---|---|
| Berry and plant attributes[1/] | 'Star' | 'Camellia' | 'TH-917' |
| Berry size | 7.4 ± 0.2 | 8.6 ± 0.2 | 7.5 ± 0.2 |
| Berry scar | 6.9 ± 0.1 | 7.0 ± 0.1 | 7.1 ± 0.1 |
| Berry color | 7.1 ± 0.1 | 7.9 ± 0.2 | 7.6 ± 0.2 |
| Berry firmness | 7.2 ± 0.1 | 7.2 ± 0.1 | 7.5 ± 0.3 |
| Berry flavor | 7.1 ± 0.1 | 7.4 ± 0.2 | 7.5 ± 0.3 |
| Cropping | 6.8 ± 1.1 | 7.9 ± 0.2 | 6.4 ± 0.4 |
| Plant vigor | 8.5 ± 0.3 | 9.8 ± 0.1 | 8.4 ± 0.3 |
| Date of 50% flowering | March 13 | March 25 | March 25 |
| Date of 50% ripening | May 25 | May 31 | May 30 |
| Fruit development period (days) | 73.3 ± 10.4 | 67.3 ± 4.8 | 65 ± 1.9 |

[1/]Values are means ± the standard error with n = 5.

TABLE 3

Yield and berry weight, firmness, and Brix for 'Star' and 'Camellia' cultivars and 'TH-917' grown in Griffin, GA during 2010-2013.

| Year | 'Star' | 'Camellia' | 'TH-917' |
|---|---|---|---|
| | Yield (lbs/bush)[1/] | | |
| 2011 | 12.7 ± 3.6 | 9.7 ± 0.9 | 10.0 ± 0.7 |
| 2012 | 11.7 ± 2.3 | 10.5 ± 0.8 | 17.0 ± 1.0 |

TABLE 3-continued

Yield and berry weight, firmness, and Brix for 'Star' and 'Camellia' cultivars and 'TH-917' grown in Griffin, GA during 2010-2013.

| Year | 'Star' | 'Camellia' | 'TH-917' |
|---|---|---|---|
| 2013 | 3.9 ± 0.6 | 15.9 ± 1.0 | 15.5 ± 0.8 |
| Avg | 9.4 | 12.0 | 14.2 |
| | Berry wt. (g/berry)[2/] | | |
| 2010 | 1.53 ± 0.09 | 2.94 ± 0.12 | 1.90 ± 0.10 |
| 2011 | 1.20 ± 0.04 | 1.97 ± 0.11 | 1.80 ± 0.08 |
| 2012 | 1.80 ± 0.07 | 1.60 ± 0.09 | 1.55 ± 0.05 |
| 2013 | 1.79 ± 0.06 | 2.56 ± 0.10 | 1.76 ± 0.03 |
| Avg | 1.58 | 2.28 | 1.75 |
| | Firmness (g/mm)[2/] | | |
| 2010 | 196 ± 4 | 150 ± 2 | 165 ± 4 |
| 2011 | 206 ± 6 | 166 ± 3 | 173 ± 3 |
| 2012 | 190 ± 5 | 164 ± 4 | 168 ± 2 |
| 2013 | 191 ± 5 | 150 ± 2 | 166 ± 2 |
| Avg | 196 | 157 | 168 |
| | Brix (%)[3/] | | |
| 2012 | 13.9 ± 0.6 | 14.5 ± 0.4 | 12.0 ± 0.3 |
| 2013 | 13.5 ± 0.5 | 13.3 ± 0.3 | 13.3 ± 0.7 |
| Avg | 13.7 | 13.9 | 12.7 |

[1/]Values are means ± the standard error with n = 3.
[2/]Values are means ± the standard error with n = 3 (each sample derived from 25 berry avg).
[3/]Values are means ± the standard error with n = 3 (each sample derived from 5 berry composite).

BRIEF DESCRIPTION OF THE FIGURES

The accompanying photographic illustration shows typical specimens in full color of the foliage, flowering, and fruit of the new variety 'TH-917'. The colors are as nearly true as is reasonably possible in a color representation of this type.

'TH-917' BOTANICAL DESCRIPTION

Figure 1:
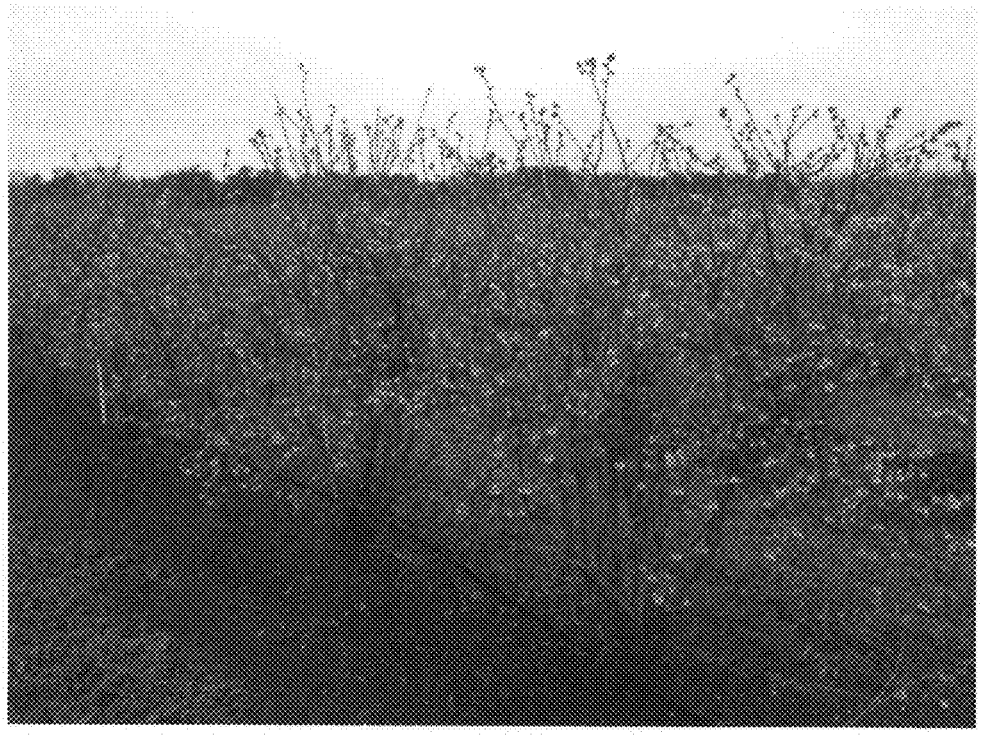
FIG. 1 is a photograph of the new variety 'TH-917' during flowering in Griffin, Ga.
Figure 2:
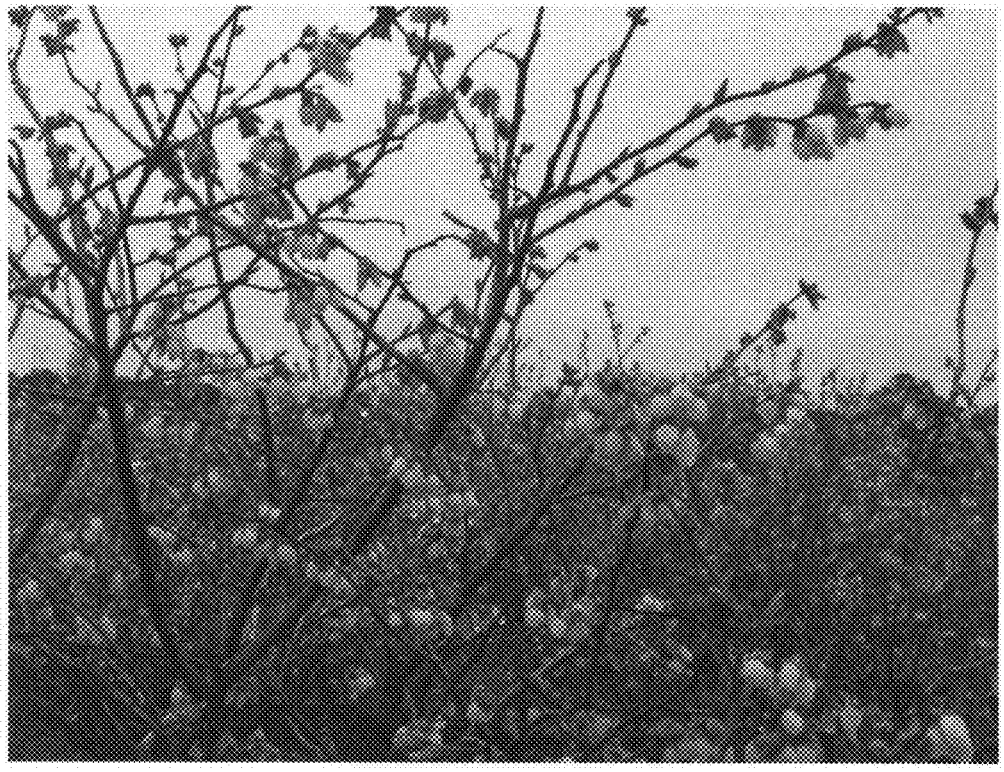
FIG. 2 is a close up photograph of the new variety 'TH-917' during flowering in Griffin, Ga.
Figure 3:
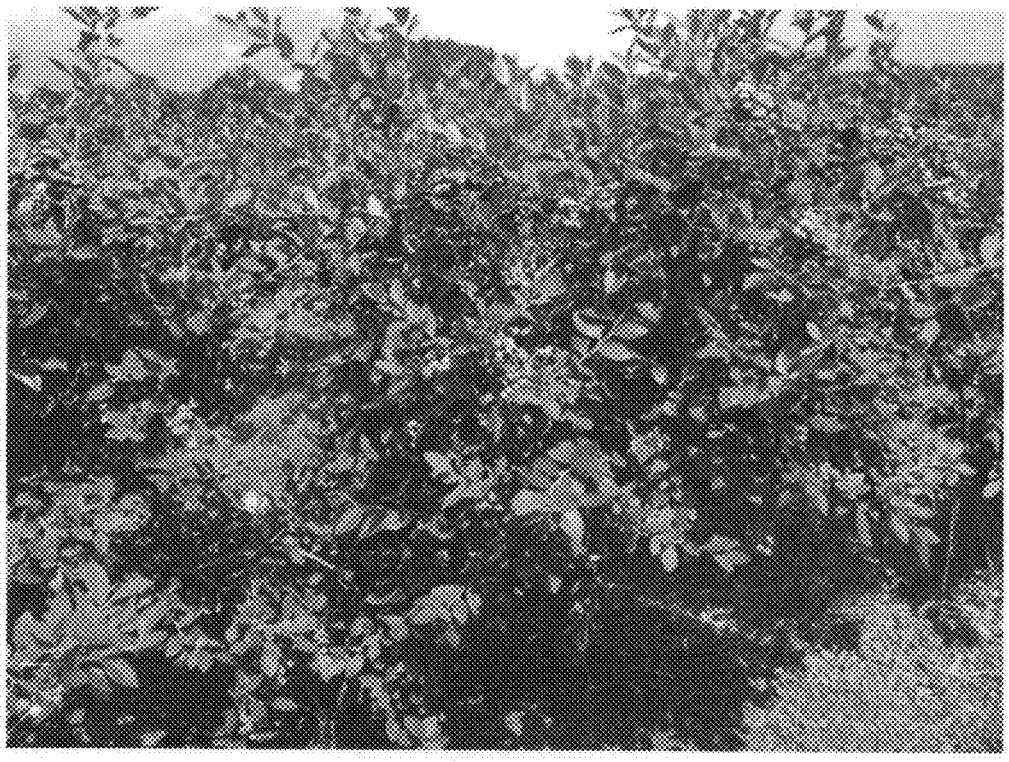
FIG. 3 is a photograph of new variety 'TH-917' during fruit ripening in Griffin, Ga.
Figure 4:
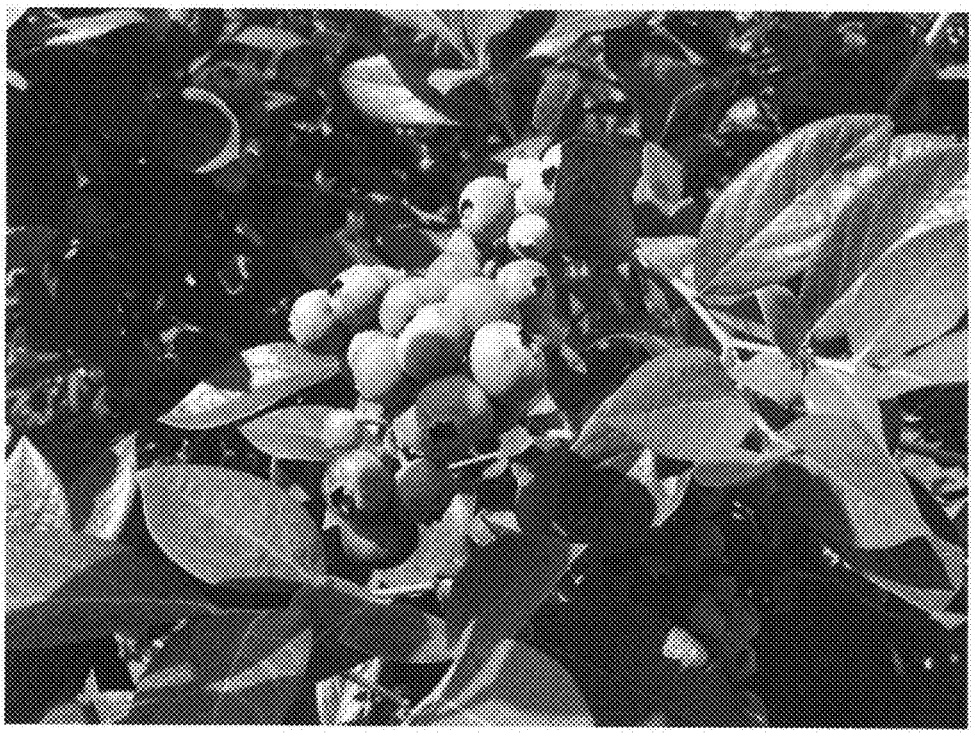
FIG. 4 is a close up photograph of the new variety 'TH-917' fruit clusters.
Figure 5:
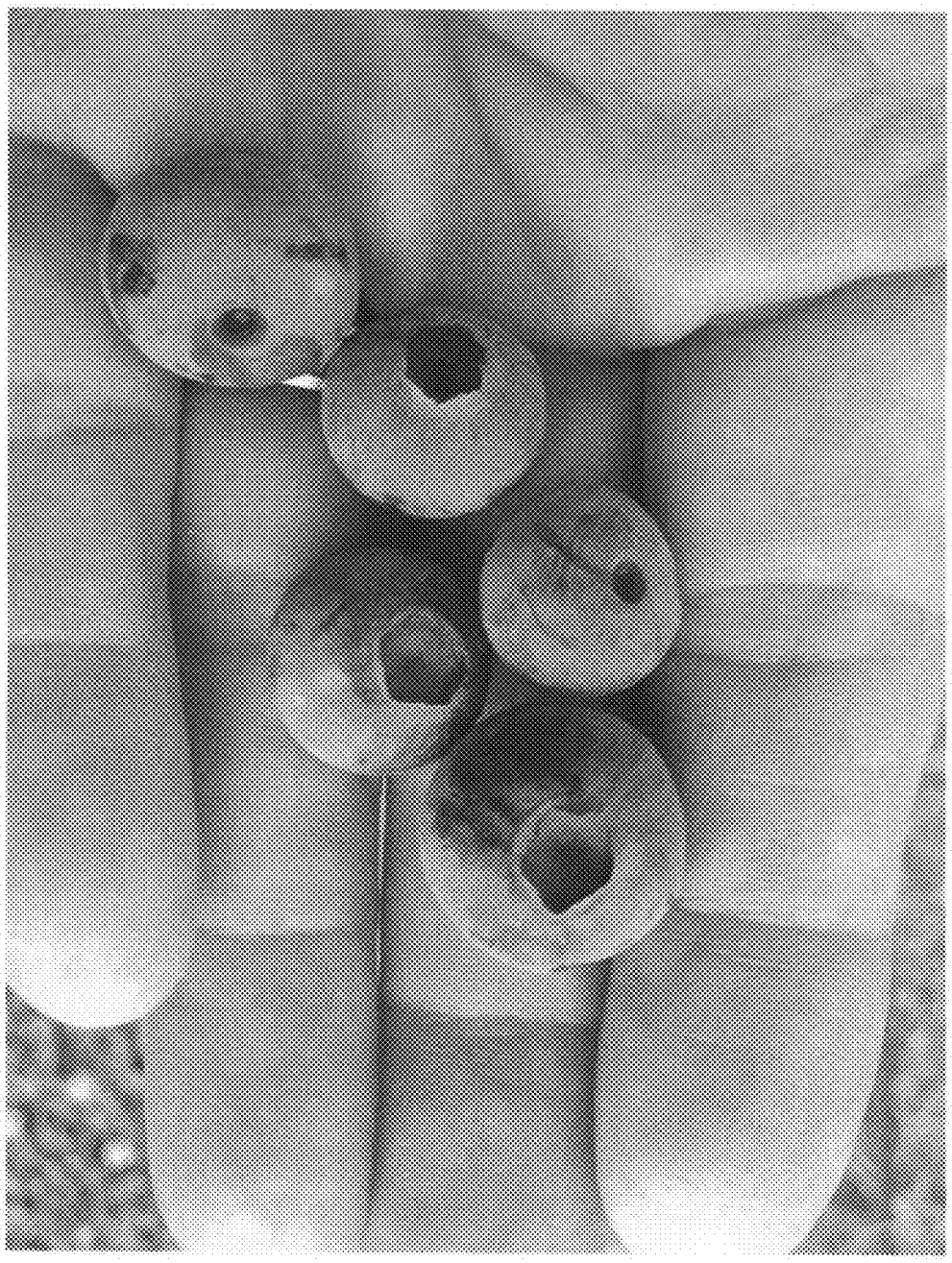
FIG. 5 is a close up photograph of typical fruit of the new variety.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following is a detailed description of the botanical and pomological characteristics of the new variety 'TH-917'. Where dimensions, sizes, colors, and other characteristics are given, it is to be understood that such characteristics are approximations and averages set forth as accurately as practicable. The descriptions reported herein are largely from specimen plants grown in Alapaha and Griffin, Ga., with supplemental irrigation. Plants were about 3 to about 6 years old.

PLANT

Size: 1.4 to 1.8 m tall by about 4 years of age. Plants grown under highly productive soil and fertility conditions have exceeded 2.0 m tall in 4 years. The plant crown, or base, is narrow, typically 20 to 25 cm in diameter. Upper portion of plant canopy exceeds 1.3 m in diameter by 3 to 4 years.

Growth habit: Strongly upright, with 1 to 3 main canes arising from the crown, and multiple branching of shoots (2 to 3 per cane) from those canes at 10 cm or less above the soil surface.

Growth: Highly vigorous.

Productivity: Very good crop and yield, averaging 10 to 18 lbs of fruit per plant each year for plants 4 years and older grown under well fertilized and irrigated field conditions.

Hardiness: Similar to other southern highbush cultivars such as 'Star' and 'Camellia'.

Chilling requirement: 500-550 hours of temperatures at or below 7° C. (about 45° F.) to induce normal leafing and flowering during the spring under conventional production systems. The chill requirement is more than the male parent 'Millennia' (350 hours of chilling required) but more similar to the female parent 'TH-653' (non-patented breeding selection; estimated 500-600 hours of chilling required).

Leafing: Plants tend to break sufficient leaf buds simultaneously with, or shortly after, anthesis.

Canes:

*Diameter.*—30 to 50 mm for base of main canes that are about 4 years old and older. 10 to 15 mm in about 2 year old wood. 5 to 10 mm in current season wood.

*Color.*—Brown RHS N200D for base of canes that are about 4 years old and older. Yellow-Green RHS 145A to Greyed-Orange RHS 165A in about 2 year old wood. Yellow-Green RHS 145B to 145C in current season wood.

Fruiting wood: Moderate number of twigs 10 to 20 cm in length, with internode lengths of 20-25 mm common.

Disease resistance: No exceptional disease resistance or susceptibility observed; typical for southern highbush 'Star' and 'Camellia' cultivars.

FOLIAGE

Leaf color: Healthy mature leaves.

*Top side.*—Green RHS 137C.

*Under side.*—Green RHS 138C.

Leaf arrangement: Alternate, simple.

Leaf shape: Elliptic.

Leaf surface: Glaucous.

Leaf margins: Nearly entire, smooth.

Leaf venation: Pinnate with slight netting.

Leaf apices: Broadly acute.

Leaf bases: Acute.

Leaf dimensions:

*Length.*—55.0 to 65.0 mm.

*Width.*—30.0 to 35.0 mm.

Petioles: Small.

*Length.*—3.0 to 4.0 mm.

*Width.*—1.5 to 2.0 mm.

*Color.*—Yellow-green RHS 145B.

FLOWERS

Date of 50% anthesis: March 10 in southern Georgia and March 25 in middle Georgia (5 year average).

Flower shape: Urceolate.

Flower bud number: High to very high, averaging 5 to 7 buds per fruiting shoot.

Flowers per cluster: 7 to 10 common.

Flower fragrance: None.

Corolla:

*Color.*—White RHS 155C (open flower).

*Length.*—9.0 to 10.0 mm.

*Width.*—7.0 to 8.0 mm.

*Aperture width.*—3.0 to 3.5 mm.

Flower peduncle:

*Length.*—10.0 to 15.0 mm.

*Color.*—Yellow-Green RHS 145C, with a trace of Red-Purple RHS 59C often observed.

Flower pedicle:

*Length.*—4.5 to 6.0 mm.

*Color.*—Green RHS 139D.

Calyx (with sepals):

*Diameter.*—6.0 to 7.0 mm.

*Color.*—Green RHS 138B to Green RHS 139D.

Stamen:

*Length.*—6.0 to 7.0 mm.

*Number per flower.*—10.

*Filament color.*—Yellow-Green RHS 145D.

Style:

*Length.*—8.0 to 9.0 mm.

*Color.*—Yellow-Green RHS 145C.

Pistil:

*Length.*—10.0 to 12.0 mm.

*Ovary color (exterior).*—Green RHS 138C.

Anther:

*Length.*—4.0 to 4.5 mm.

*Number.*—10.

*Color.*—Greyed-Orange RHS 165B.

Pollen:

*Abundance.*—High.

*Color.*—Orange-White RHS 159A.

Self-compatibility: The cultivar has a moderate degree of self-compatibility.

FRUIT

Date of 50% maturity: May 17 in southern Georgia and May 30 in middle Georgia (5 year average).

Fruit development period: 62 to 70 days.

Berry color:

*With wax.*—Violet-Blue RHS 97B.

*With wax removed.*—Black RHS 202A.

Berry surface wax abundance: High.

Berry flesh color: Green-White RHS 157B.

Berry weight:

*First harvest.*—1.8 g to 2.4 g.

*Second harvest.*—1.6 g to 1.9 g.

Berry size:

*Height from calyx to scar.*—10.0 to 13.0 mm.

*Diameter.*—15.0 to 18.0 mm.

Berry shape: Semi-spherical.

Fruit stem scar: Small to medium, medium-dry, with little or no tearing at harvest.

Calyx: Depth 2.0 to 3.0 mm; width 5.0 to 7.0 mm; sepals slightly showing and most often turn slightly inward when present.

Berry firmness: Moderately firm.

Berry flavor and texture: Sweet, mildly acidic flavor; smooth texture, somewhat crisp.

Storage quality: Good to very good.

Suitability for mechanical harvesting: Likely suitable.

Uses: Can be used as fresh fruit for shipping, but also customer-pick and processing markets.

SEED

Seed abundance in fruit: Medium, with 10 to 20 fully developed seeds per berry.

Seed color: Greyed-Orange RHS 165B.

Seed dry weight: 42.8 mg per 100 seeds.

Seed size: 1.0 to 1.2 mm long; 0.4 to 0.6 mm wide for fully developed seeds.

What is claimed is:

1. A new and distinct variety of southern highbush blueberry plant named 'TH-917', substantially as illustrated and described herein.

* * * * *